US008088929B2

(12) United States Patent
Losson et al.

(10) Patent No.: US 8,088,929 B2
(45) Date of Patent: *Jan. 3, 2012

(54) METHOD FOR PRODUCING J AGGREGATES (75) Inventors: Myriam Losson, Corcelles (CH); Raphaël Pugin, Auvernier (CH); Rolf Steiger, Le Mouret (CH); Véronique Monnier, La Chaux-de-Fonds (CH); Rino E. Kunz, Herrliberg (CH); Stanley Ross, Epalinges (CH)

(73) Assignee: CSEM Centre Suisse d'Electronique et de Microtechnique SA - Recherche et Developpment, Neuchatel (CH)

( * ) Notice: Subject to any disclaimer, the term of this patent is extended or adjusted under 35 U.S.C. 154(b) by 624 days.

This patent is subject to a terminal disclaimer.

(21) Appl. No.: 12/094,038

(22) PCT Filed: Nov. 10, 2006

(86) PCT No.: PCT/EP2006/068340
§ 371 (c)(1),
(2), (4) Date: Jun. 2, 2008

(87) PCT Pub. No.: WO2007/057356
PCT Pub. Date: May 24, 2007

(65) Prior Publication Data
US 2008/0279500 A1 Nov. 13, 2008

(30) Foreign Application Priority Data

Nov. 16, 2005 (CH) .................................. 1838/05

(51) Int. Cl.
C09B 67/02 (2006.01)
G01N 21/64 (2006.01)
G02B 6/12 (2006.01)
C09K 11/06 (2006.01)

(52) U.S. Cl. ............ 548/219; 385/14; 385/141; 427/337

(58) Field of Classification Search .................. None
See application file for complete search history.

(56) References Cited

U.S. PATENT DOCUMENTS

| 6,977,178 | B2 * | 12/2005 | Hodge et al. | 436/94 |
| 7,261,875 | B2 * | 8/2007 | Li et al. | 424/1.69 |
| 7,824,617 | B2 * | 11/2010 | Steiger et al. | 422/68.1 |
| 2004/0023248 | A1 * | 2/2004 | O'Malley | 435/6 |
| 2005/0191643 | A1 * | 9/2005 | Haugland et al. | 435/6 |

FOREIGN PATENT DOCUMENTS

| CH | EP 1 085 315 A1 | 3/2001 |
| DE | 19855180 * | 5/2000 |
| EP | 1 081 557 A1 | 3/2001 |

OTHER PUBLICATIONS

Place, Ileana. et al., "Layered Nanocomposites of Aggregated Dyes and Inorganic Scaffolding", J. Phys. Chem. A, 107(18), 3169-3177, 2003.*
Esfand, Roseita et al., "Poly(amidoamine) (PAMAM) Dendrimers: From Biomimicry to Drug Delivery and Biomedical Applications", DDT, 6(8), 427-436, Apr. 2001.*
Steiger, Rolf et al., "J-Aggregation of Cyanine Dyes by Self-Assembly", Colloids and Surfaces B: Biointerfaces, 74, 484-491, 2009.*
Bumb, A. et al., "Preparation and Characterization of a Magnetic and Optical Dual-Modality Molecular Probe", Nanotechnology, 21(17), 175704 (9pp), 2010.*
Kometani, Noritsugu et al., Luminescence Properties of the Mixed J-Aggregate of Two Kinds of Cyanine Dyes in Layer-by Layer Alternate Assemblies:, Journal of Physical Chemistry B, 104(41), 9630-9637, 2000.*
Talanov, Vladimir S. et al., "Dendrimer-Based Nanoprobe for Dual Modality Magnetic Resonance and Fluorescence Imaging", Nano Letters, 6(7), 1459-1463, 2006.*
Talanov , Vladimir S. et al., "Dendrimers for Dual Imaging Modalities: Combining Magnetic Resonance and Optical Fluorescent Imaging", $37^{th}$ ACS Meeting, Middle Atlantic Regional Meting (May 22-25, 2005), Abstract No. 409.*
M. Losson: "Self-organizing properties of dendrimers and potential applications; These pur l'obtention du titre de Docteur es Sciences" Oct. 24, 2005, Universite de Neuchatel; Faculte des Sciences, Neuchatel, XP002417620, the whole document.
H. Tokuhisa et al: "Preparation and Characterization of Dendrimer Monolayers and Dendrimer-Alkanethiol Mixed Monolayers Adsorbed to Gold" Journal of the American Chemical Society, vol. 120, 1998, pp. 4492-4501, XP002417618.
R. Steiger et al.: "Physical-Chemical Properties of Organized Sensitizer Molecules" Journal of Imaging Science, vol. 32, 1988, pp. 64-81, XP008074432.
M. Wells et al: "Interactions between Organized, Surface-Confined Monolayers and Vapor-Phase Probe Molecules. 10. Preparation and Properties of Chemically Sensitive Dendrimer Surfaces" Journal of American Chemical Society, vol. 118, No. 16, 1996, pp. 3988-3989.
D.M. Sturmer: "Syntheses and Properties of Cyanine and Related Dyes" published in the book "Chemistry of Heterocyclic Compounds: Special Topics" edited by A. Weissberger et al., 1977 (Wiley Interscience, New York) vol. 30, pp. 441-601.
H. Kuhn et al. "Chromophore Coupling Effects" published in a book entitled "J-aggregates" by T. Kobayashi, pp. 1-40, ISBN 981-02-2737-X.

* cited by examiner

Primary Examiner — Fiona T Powers
(74) Attorney, Agent, or Firm — Young & Thompson (57) ABSTRACT

A method for producing special supramolecular assemblies of colorants, in particular cyanine dyes, called J aggregates consists in depositing a monolayer of dendrimers on a support and subsequently in deposing cyanines in solution for forming the organized monolayer of J aggregates. The method can be used for producing a secondary light source for injecting light into a waveguide from a light energy received from a primary light source emitting at different wavelength. The secondary source, which consists of the J aggregates incorporating energy acceptors, can also be integrated into an optical device incorporating the waveguide.

28 Claims, 8 Drawing Sheets

METHOD FOR PRODUCING J AGGREGATES

TECHNICAL FIELD

The present invention relates to the field of nanotechnology and more specifically relates to special supramolecular assemblies of dyes, notably from the family of cyanines, called J aggregates. In particular, the invention relates to a method with which such J aggregates may be made very simply. It also relates to an assembly comprising a layer of J aggregates and to optical devices applying the J aggregates obtained according to the method of the invention.

In the present document, the term of cyanines will both encompass cyanines and mero-cyanines and their derivatives, as defined in the article of D. M. Sturmer published in the book "Chemistry of heterocyclic compounds: special topics", Volume 30, pp 441-601, edited by A. Weissberger and B. W. Rossiter, 1977 (Wiley Interscience, New York), and including structure examples which are given in FIGS. 2a and 2b, 3, 9, 10 and 14, respectively.

J aggregates are self-arrangements of cyanine molecules which form very ordered assemblies and the structural organizations of which are of the crystalline type. A description of the J aggregates and their properties may be found in the article by H. Kuhn et al. in a book entitled "J-aggregates" by T. Kobayashi, ISBN 981-02-2737-X. Because of the quasi-faultless organization of the J aggregates, they have remarkable properties. Thus, it was observed that irradiation of a two-dimensional monolayer of J aggregates causes the formation of an exciton which is capable of propagating in the whole of this monolayer at high speed, typically 2 km/s, in a coherent way and with extremely small energy losses.

State of the Art

The astounding properties of J aggregates were observed for the first time during the 1930s. Since then, numerous applications have been proposed as an experiment, demonstrating the extent of the possibilities provided by the J aggregates. For example, light concentration systems for solar devices and sensors, components for non-linear optical systems, fast optical recording systems, etc., may be mentioned.

However, these various applications have for the moment remained at an experimental level. Indeed, it is very difficult to succeed in organizing cyanine monomers so that they form J aggregates without any defects and in a monolayer and this reproducibly. To the knowledge of the applicant, there is no technique with which these aggregates may be made in a sufficiently simple, fast and reproducible way for allowing them to be applied industrially.

Among the numerous techniques which have been tried up to now and published in the literature, mention will be made of that of Langmuir-Blodgett (see on this subject, the article of R. Steiger and F. Zbinden in Journal of Imaging Science, Vol. 32, 1988, p. 64), which consists of filling with ultra-pure water a Teflon tank provided with a mobile barrier positioned at the surface of the liquid. Amphiphilic cyanine molecules are deposited at the surface and the barrier is moved very slowly until these molecules form an ordered monolayer at the surface of the liquid. According to this method, it is possible that the thereby obtained film may be transferred on a support by capillarity. Of course, it is understood that this technique is very delicate and slow and that it cannot be reproduced in order to provide J aggregates in an industrial amount. However, J aggregates of very high quality may be obtained with the latter technique, i.e. the organization of which has quasi no defect. Hence, the physico-chemical characteristics of the J aggregates made by this method, may be considered as references.

In a different and more recent approach, it was attempted to deposit cyanine molecules on supports forming "template matrices" with which the phenomenon of aggregation of the molecules may be guided and controlled. The term "template" is currently used by one skilled in the art for describing this type of matrix. Thus, supports based on polymers, biopolymers, polysoap, micelles, polyacrylic acids, liposomes or alginates have been tested, but with no success. Indeed, the obtained aggregates are poorly defined, in the sense that the order of the arrangement is not guaranteed at a molecular scale, and they either include several layers, or are unstable.

The object of the present invention is to propose a simple, fast and effective method, with which stable and high quality J aggregates may be obtained in a reproducible way, i.e. the physico-chemical characteristics of which are comparable with reference values.

DISCLOSURE OF THE INVENTION

More specifically, the invention relates to a method for making J aggregates, comprising the following steps:
  i. providing a support cleaned beforehand,
  ii. depositing on the support, a solution of dendrimer molecules capable of interacting with it in order to form a monolayer having on its outer face, a regular and organized structure, and
  iii. covering the obtained assembly with a solution of cyanines reacting with said dendrimer molecules in order to be self-arranged into J aggregates.

The invention also relates to an assembly formed with a support, an organized layer of dendrimer molecules and, on the organized layer of these molecules, a monolayer of molecules from the family of cyanines organized into J aggregates.

SHORT DESCRIPTION OF THE DRAWINGS

The invention will be better understood upon reading the description which follows, made with reference to the appended drawings wherein.

The different spectra show the absorption or the emission, versus the incident or emitted wavelength.

EMBODIMENT(S) OF THE INVENTION

An exemplary method for making a particular J aggregate will be described in detail hereafter, as a non-limiting illustration of the invention. As this will be understood, the method essentially consists of coating a support prepared beforehand with a template matrix, and then of depositing on this matrix, the cyanine molecules in order to form J aggregate.

Preparation of the Support

A glass support of the borosilicate type forming a plate of about 3 cm by 1 cm, is cleaned, for example by immersion in a so-called Piranha solution consisting of $H_2SO_4$ and of $H_2O_2$, in a proportion of 2 to 1, at 120° C. for 10 minutes. Next, the support is rinsed with ultra-pure water and dried under a stream of nitrogen. The support is then activated by treatment with oxygen plasma, for 3 minutes. This plasma is generated between two capacitor plates, by inducing a radiofrequency current through the plates. The highly energetic particles of the plasma degrade the possible organic residues remaining on the support into volatile molecules which are evacuated. The support is then perfectly cleaned and ready for the following steps.

Deposit of the Template Matrix ("Templated")

Figure 1:
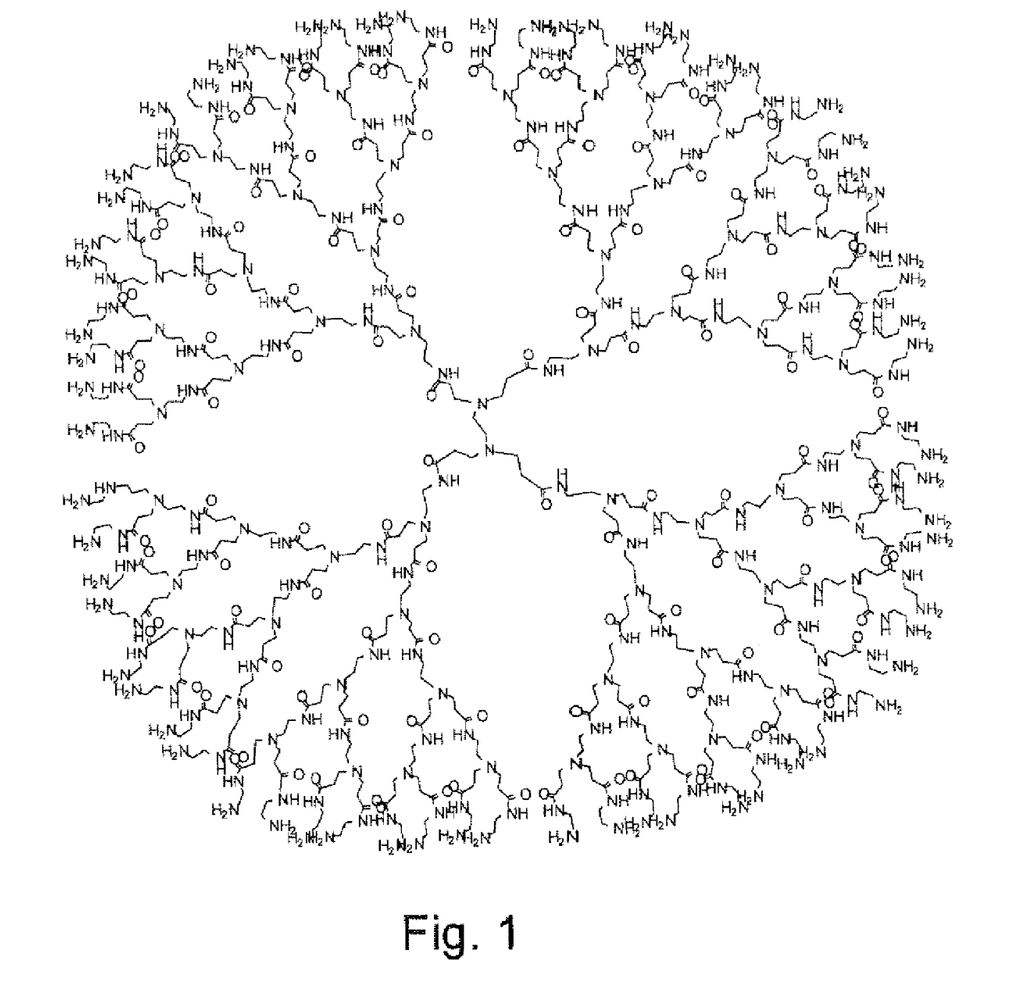
FIG. 1 illustrates the structure of a dendrimer (PAMAM) of generation 4 (G4)
Figure 2A:
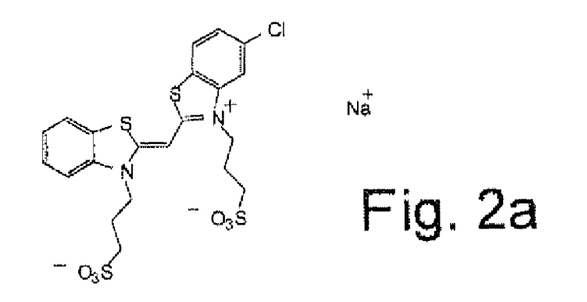
FIGS. 2a and 2b give an example of cyanines and mero-cyanines, respectively.
Figure 2B:
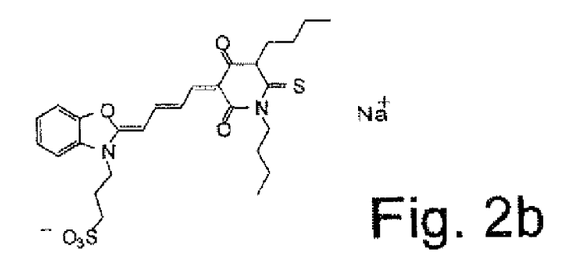
Figure 3:
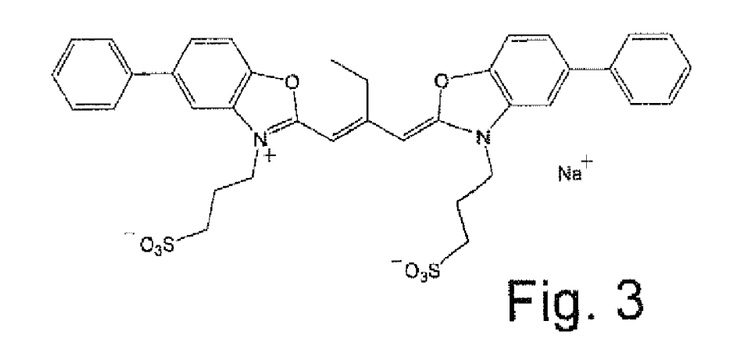
FIG. 3 shows the structure of Myline 1.

Typically, a template matrix is made on the basis of dendrimers, i.e. macromolecules, each consisting of monomers which associate with each other according to an arborescent process around a plurifunctional core. The arborescent construction is carried out by repeating a same sequence of reactions until a new generation and an increasing number of identical branches are obtained at the end of each reaction cycle. A dendrimer example, a polyamido-amide of the fourth generation, designated as PAMAM G4, is illustrated in FIG. 1.

The dendrimers have the advantage of being monodisperse and of having strictly controlled structure, geometry and stoichiometry. Indeed, as the reaction scheme of their preparation is clearly defined, each of the molecules of a given dendrimer is identical with another. The number of functions, the charge density, the surface and the occupied volume, are known for a dendrimer molecule. The table hereafter gives a few examples of dendrimers as well as their properties.

| | Number of peripheral functions | Diameter (nm) | Outer surface ($nm^2$) | Surface density of the functional groups (per $nm^2$) |
|---|---|---|---|---|
| PAMAM G1 | 8 | 2.2 | 3.8 | 2.11 |
| PAMAM G4 | 64 | 4.5 | 15.9 | 4.02 |
| PAMAM G6 | 256 | 6.7 | 35.2 | 7.26 |

The support prepared during the preceding step is immersed for 18 hours in an ethanol solution of PAMAM G4 concentrated to $1.10^{-4}M$. By the interactions between the support and the PAMAM, the latter is absorbed at the surface of the support in order to form on the latter a homogenous monolayer (see in particular, the article of H. Tokuhisa et al., J. Am. Chem. Soc., 1998, 120, 4492).

In the example shown, the reactions between the PAMAM and the support are of the acidobasic type between the amine functions of the PAMAM and the silanol groups of the glass, but other types of interactions (electrostatic interactions, Van der Waals bonds, metal-ligand type interactions, etc. . . . ) may also be at play, depending on the different selected supports, as this will be explained hereafter. Moreover, other deposition techniques may be used in order to obtain a homogenous monolayer. Among these techniques, mention may be made of: "spin coating" or deposition on a rotating sample, printing, "spraying" or pulverization, etc.

Next, the support is rinsed with pure ethanol in order to remove the PAMAM molecules not bound to the support. Finally, the support is dried under a stream of nitrogen.

An assembly consisting of a support, in this case in glass, covered with a regular monolayer of dendrimers of PAMAM according to the example, is thereby obtained J Aggregate Formation The cyanine used for forming the J aggregate is [5,5'-diphenyl-dibenzoxazolo-N,N'-propylsulfonate]-9-ethyl trimethine cyanine (called Myline 1). As these cyanines are sensitive to light, exposing them to light should absolutely be avoided, both during the preparation of the reagent and during the reaction. The cyanine is put into solution in acetone at a concentration of $7.10^{-4}M$. The mixture is magnetically stirred for 2 hours in order to guarantee total solubilization of the reagent.

The proposed cyanine is charged negatively. Thus, in order to allow it to interact with the PAMAM deposited on the support, the latter is immersed beforehand in an acid solution, typically hydrochloric acid at a pH of 3.5 in order to protonate all the amines of the PAMAM. The thereby activated support is then immersed in the above cyanine solution. The immersion time is comprised between a few seconds and a few minutes, and will be discussed hereafter. Thus, the support is rinsed with pure acetone and dried under a stream of nitrogen.

An assembly consisting of a support, in this case in glass, covered with a regular monolayer of dendrimers, of PAMAM according to the example and with a monolayer of J aggregates, is thereby obtained.

Results

Figure 4A:
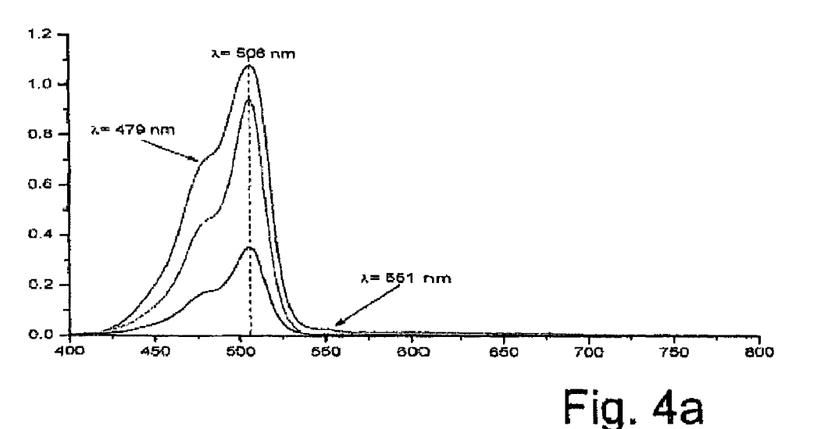
FIGS. 4a and 4b compare the absorption spectra of Myline 1 at different concentrations and of J aggregates of Myline 1, respectively, FIG. 5 provides absorption and emission spectra of J aggregates of Myline 1 on a PAMAM G4 matrix.
Figure 4B:
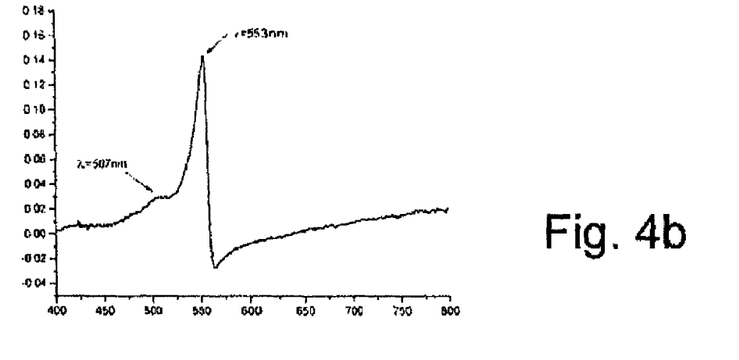

The assembly obtained above, particularly the cyanine layer, is analyzed by means of a UV-visible spectrophotometer. The obtained spectrum with an immersion time of 12 minutes is shown in FIG. 4b, to be compared with that of the Myline 1solution used as a reagent, illustrated in FIG. 4a.

The study of this spectrum (FIG. 4a) shows three peaks for the reagent, at 479 nm, 506 nm, and 551 mm described in the literature as respectively corresponding to the absorption peaks of the dimmer, of the monomer and of the J aggregate of Myline 1. The spectrum of the Myline 1 layer deposited on the support shows that there is no longer any dimmer (absence of a peak at 479 nm) and almost no longer any monomer (a weak peak at 507 nm). On the other hand, the signal corresponding to the J aggregate is very intense, which means that the layer almost exclusively consists of J aggregates. The wavelength of the J aggregate peak obtained according to the above method and for reference samples obtained by the Langmuir-Blodgett technique are remarkably in agreement, thereby confirming the regularity and quality, i.e. the high organization and the large homogeneity of the produced J aggregate.

Figure 5:
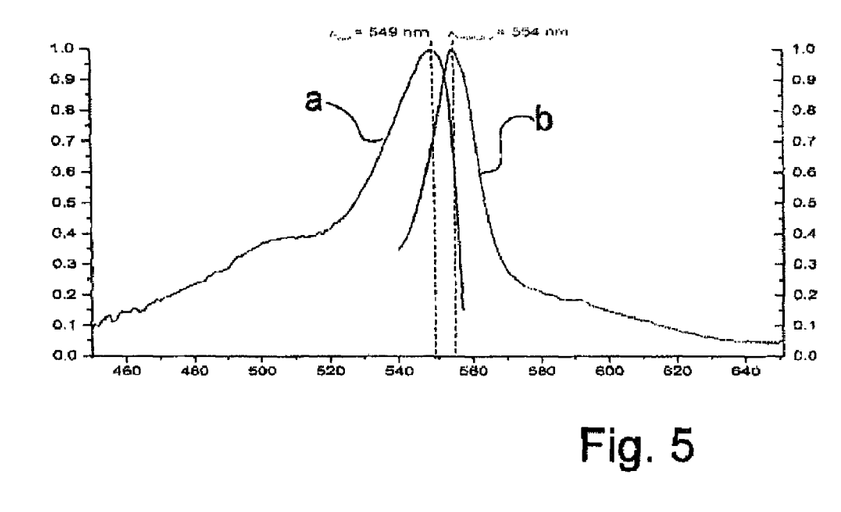

The quality of the organization and of the homogeneity of the formed J aggregate is confirmed by comparing the fluorescence emission and absorption wavelengths of the assembly obtained above. The spectrum is shown in FIG. 5. The absorption peak a appears at a wavelength of 549 nm, whereas the emission peak b appears at 554 nm. This small difference shows that the layer is homogenous and perfectly organized at a molecular level.

Figure 6:
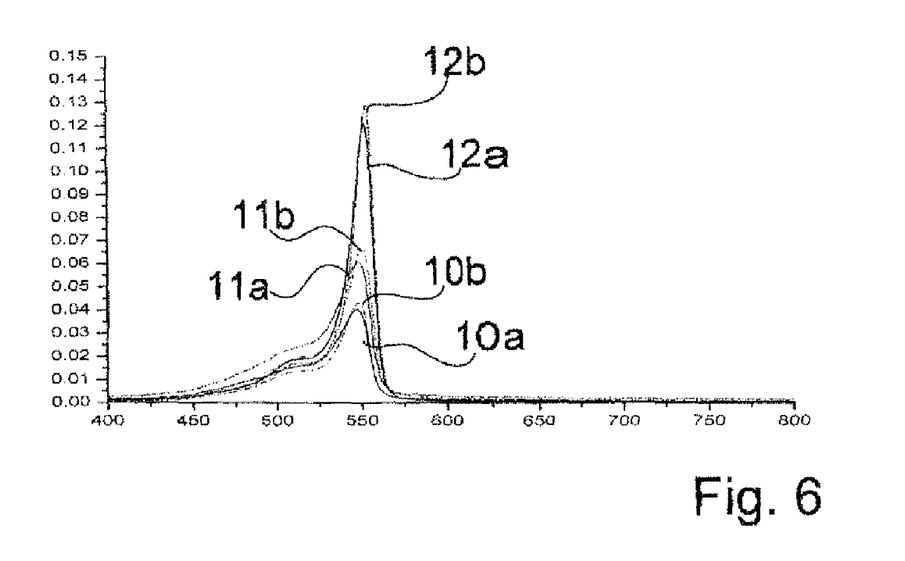
FIG. 6 shows the absorption spectra of J aggregates on PAMAM G1, G4 and G6 matrices, made just after and 14 weeks after forming the J aggregates, FIG. 7 proposes compared absorption spectra of J aggregates formed on PAMAM G4 matrices and on polylysine matrices.

An important parameter which indicates that the method described above provides significant progress with a view to be able to apply the J aggregates industrially, is the time stability of the formed aggregates. FIG. 6 shows the changes in absorption for an assembly obtained according to the invention, with a glass support covered with PAMAMs of different generations G1, G4 and G6 respectively, for the spectra 10, 11 and 12. Between the different measurements, the samples are kept in darkness. The spectra indexed as a are obtained just after the reaction, whereas the spectra indexed as b were achieved 14 weeks later. It is observed that in the absence of light, the J aggregates obtained according to the method of the invention, remain remarkably organized, and even that the intensity of the peaks slightly increases. It may be believed that this effect is due to the removal of solvent traces still present just after the reaction.

In order to demonstrate the effectiveness and the benefit for using a dendrimer as compared with a polymer, a glass support was covered with a polylysine layer. This polymer includes a large number of amine functions and its capacity of self-arranging the Myline 1 molecules into J aggregates may therefore be compared with that observed for PAMAM. The assembly formed by a glass support and a polylysine layer undergoes the treatment described in the previous paragraph relating to the formation of J aggregates.

Figure 7:
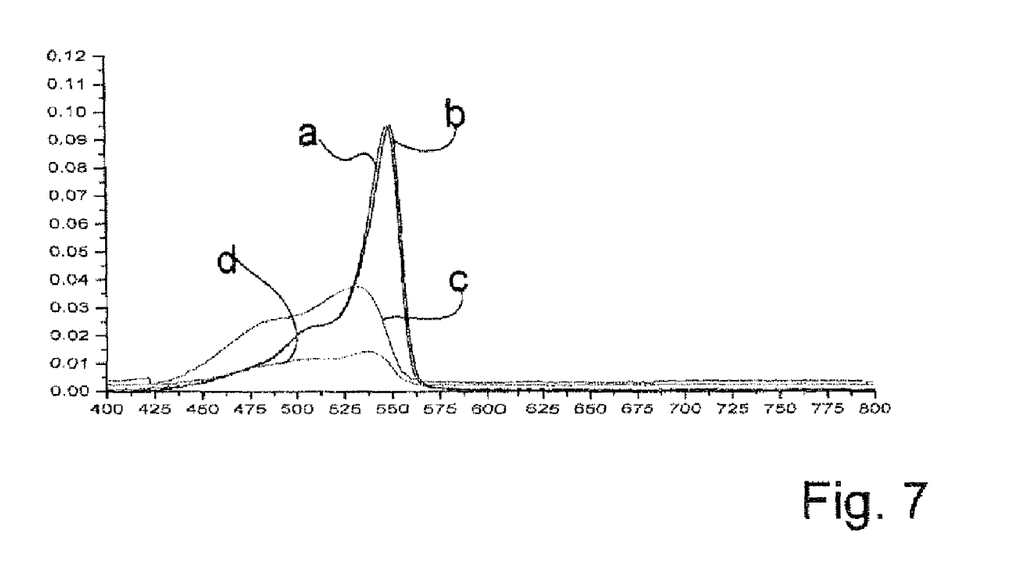

FIG. 7 illustrates the UV absorption spectra of a Myline 1 layer deposited under the following conditions:
  a: deposited on a PAMAM G4 layer, spectrum completed after the last rinse;
  b: deposited on a PAMAM G4, spectrum completed after the last rinse is performed with acetone;
  c: deposited on a polylysine layer, spectrum completed before the last rinse;
  d: deposited on a polylysine layer, spectrum completed after the last rinse is performed with water.

FIG. 7 shows that with a polylysine layer, the absorption peak corresponding to the J aggregate is poorly defined (between 530 and 544 nm), less intense and much wider that with a PAMAM layer. Further, the spectrum d illustrates that the cyanine molecules are not stable on the polylysine layer and that they reorganize on this surface. A contrario, this comparison proves that the dendrimer matrices, and in particular those functionalized with PAMAM, have an excellent capacity of self-arranging the cyanine molecules into stable and highly organized J aggregates and consequently with optical properties very close to the reference properties.

Other comparative tests with different molecular weights of polylysine polymers were conducted, also with different concentrations of cyanines as a reagent, without obtaining better results.

Alternatives at the Level of the Support

Other supports were used for receiving a layer of dendrimers, notably, gold layers having undergone activation by oxygen plasma as described above.

A PAMAM layer is deposited according to the method described earlier as regards a glass support. In a solvent of the alcohol type with a low molecular weight (ethanol, methanol, . . . ), PAMAM adheres with the gold layer essentially by the interactions between the peripheral primary amines of the PAMAM and the gold atoms of the surface. With the large number of these primary amines, very good adherence of PAMAM on the gold support may be obtained. In an aqueous solvent, the nature of the interactions between the PAMAM and gold is very different and essentially controlled by electrostatic attraction. Indeed, under these conditions, the peripheral amine groups tend to be protonated, positively charging the PAMAM.

Other types of support may further be contemplated, such as silicon, mica, quartz, or metal oxides, notably, or even flexible supports of the polymer or polycarbonate type, it being essential that sufficient interactions may be established between the support and the layer of dendrimers and that these interactions be of a nature allowing generation of a monolayer of dendrimers on the support. One skilled in the art, by means of simple experiments, will be able to establish other associations between supports and dendrimers, by varying the functional groups of the dendrimer or the experimental conditions for depositing the monolayer. It should also be noted that it is possible to have an intermediate adhesion layer between the support and the monolayer of dendrimers. An example of such an intermediate layer may be found in the article of M. Wells and R. M. Crooks, 3. Am. Chem. Soc. 1996, 118, 3988-3989.

Alternatives at the Level of the Template Matrix

Figure 8:
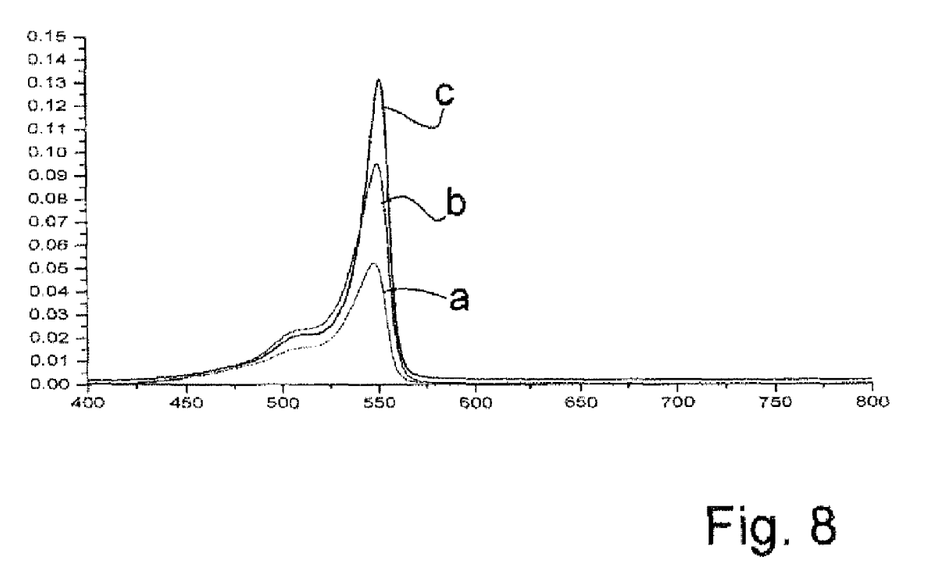
FIG. 8 shows absorption spectra of J aggregates on PAMAM G1, G4 and G6 matrices.

Different dendrimers were used and may be suitable for the aimed application. Notably, for a dendrimer of the PAMAM type, the generations 1, 4 and 6 were tested, with which by reproducing the method described above, the absorption spectra a, b, c, may respectively be obtained, as illustrated in FIG. 8. As a result of this comparison with higher generations of dendrimers, it is possible to obtain a better result, no doubt from the fact that they have a higher density of peripheral functional groups. Thus, it is likely that those PAMAMs of generations higher than 6, notably up to at least generation 10, provide excellent results.

More generally, various types of PAMAM may be used, whether they are charged positively or negatively. Other dendrimers, such as PAMAM G3.5, G4.5, . . . , Gm.5, . . . with peripheral carboxyl (COOH) or carboxylate ($COO^-$) functions, also form matrices allowing cyanine to be self-arranged into J aggregates. The essential characteristics which the molecule which forms the template matrix should have, is that its outer surface, i.e. the one forming the interface with the reaction medium when it is on the support, should be defined and regular. In addition, it should have a high density of peripheral functional groups in order efficiently interact with the support so as to be adsorbed thereto but also to react with dyes allowing them to freely self-organize. One skilled in the art will be able to carry out the required experiments for widely testing hyperbranch macromolecules, comprising dendrimers but also hyperbranch polymers, i.e. molecules including a weakly organized, polymer type portion, and a well-defined dendrimer type portion. Such hyperbranch polymers may be suitable insofar that the polymer portion is used for binding this molecule to the support, the dendrimer portion then being at the interface with the dye molecules. Within the field of the present invention, such hyperbranch polymers are supposed to be part of the family of dendrimers.

Alternatives at the Level of Cyanines

The different dyes encompassed in the definition of the cyanines given above, i.e. cyanines, mero-cyanines and their derivatives, are capable of self-arrangement in order to form J aggregates on a template matrix as defined in the preceding paragraph. Of course, the cyanine and the molecule forming the template matrix have to be selected depending on each other so that the cyanine interacts with the functional groups present at the periphery of the template matrix; for example this involves complementarity of the electric charges and similarity of the charge densities.

Figure 9:
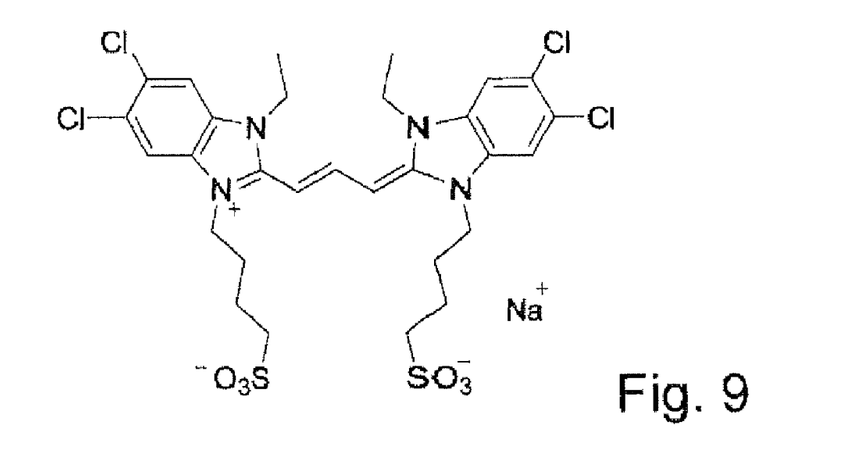
FIG. 9 shows the structure of Myline 2.

[5,5'-tetrachloro-1,1'-diethyl-dibenzoxazolo-N,N'-propionate-butyl-sulfonate] trimethine cyanine, called Myline 2 and illustrated in FIG. 9, was deposited on a PAMAM G4 template matrix deposited on a gold support. Myline 2 was used in an anionic form, in solution in acetone at $7.10^{-4}$M. As the PAMAM was protonated, as described above, the template matrix is immersed for 3 minutes in the solution of Myline 2. The formation of J aggregates was observed, confirmed by the presence of an absorption peak at 586 nm.

Figure 10:
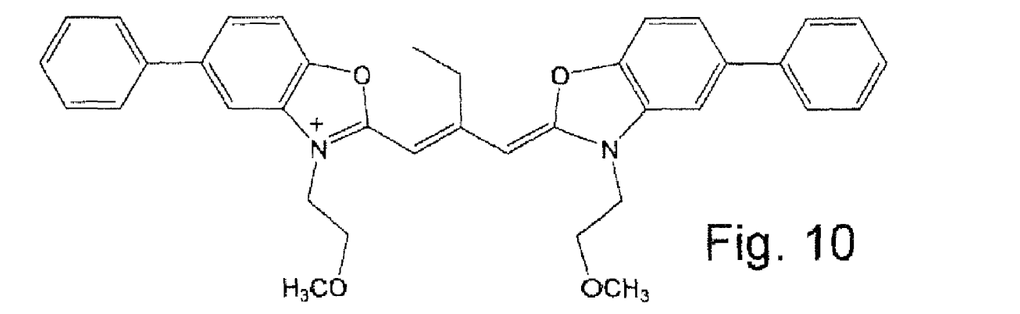
FIG. 10 shows the structure of a cyanine of the cation type.

Likewise, a cationic type of cyanine may also self-arrange in order to form J aggregates on a negatively charged template matrix. An example of such a cyanine is illustrated in FIG. 10 while a negatively charged dendrimer may for example be a PAMAM of generation, Gm.5 with carboxylate peripheral functions.

Alternatives at the Solvent Level

The solvents are involved in two steps of the reaction method. First of all, the dendrimer is dissolved in a first solvent. As already mentioned above, this first solvent preferably is an alcohol with a low molecular weight, notably methanol or ethanol.

Next, the dye is dissolved in a second solvent. In the example, the latter is acetone. Experiments conducted with a mixture of acetone and ethanol, notably a 1:1 mixture, gave good results.

Optimization of the Experimental Conditions

The numerous experiments which have been conducted for testing different alternatives capable of being applied in the method according to the invention provided identification of certain parameters allowing higher quality J aggregates to be obtained, or the method to be facilitated per se. It is quite understood that the paragraphs which follow give selections but do not form limitations aiming at excluding elements or domains which would not be comprised in the selection.

Thus, it appears that the solution of cyanines used during the formation of J aggregates gives better conversion of the cyanine molecules into J aggregates if the cyanine concentration is sufficient, i.e. close to saturation, so as to allow J aggregate kernels to be formed in the solution, which will act as germs in the subsequent growth process of the J aggregate. The value of the saturation threshold of course depends on the solvent used and on the nature of the relevant cyanine. With acetone as a solvent and cyanine Myline 1, it is therefore desirable that the concentration be equal to or larger than $7.10^{-5}$M.

Figure 11A:
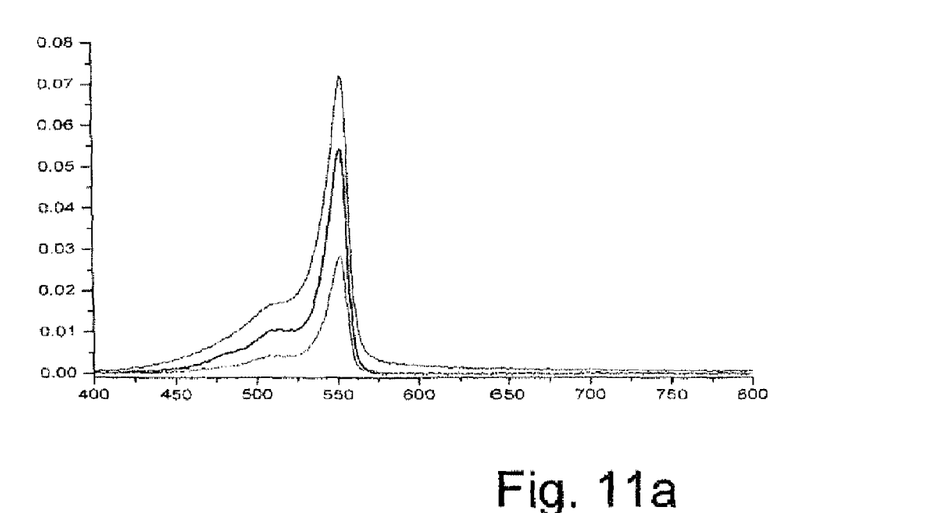
FIG. 11 illustrates the influence of the reaction temperature on the quality of the obtained 3 aggregates, by showing absorption spectra of J aggregates formed at different temperatures and deposited on PAMAM G4 in a, and on PAMAM G6 in b.
Figure 11B:
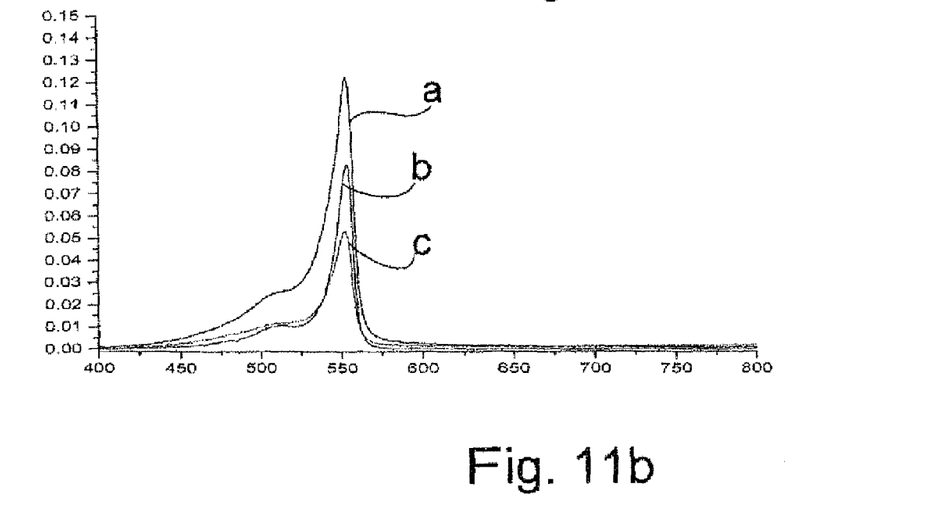

The step for forming J aggregates was conducted by setting the cyanine solution to different temperatures, i.e. to room temperature (22° C.), 40° C. and 55° C. These different tests are reproduced with a template matrix made on the basis of PAMAM G4 and PAMAM G6. The obtained absorption spectra are illustrated in FIGS. 11a and 11b, for PAMAM G4 and PAMAM G6, respectively. The curves a, b, c, correspond to the temperatures, 22, 40 and 55° C.

Figure 12A:
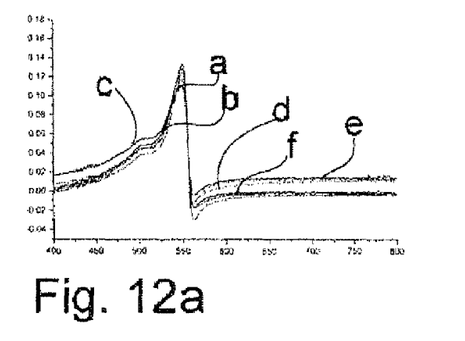
FIG. 12 shows the absorption spectra of a layer of J aggregates obtained according to the invention versus the immersion time in the Myline solution during the step for forming the J aggregates.
Figure 12B:
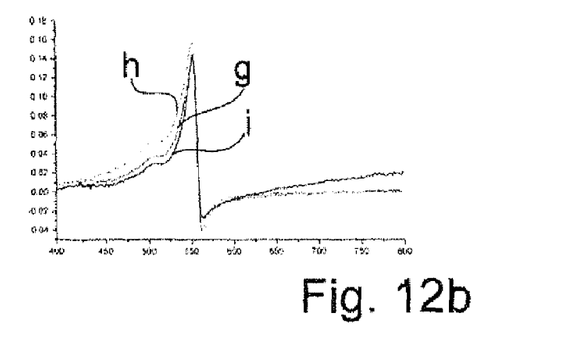

The influence of the immersion time of the support covered with the template matrix in the cyanine solution during the step for forming J aggregates was also explored. Times varying from 15 seconds to 12 minutes were tested, with a gold support covered with a layer of PAMAM G4, acidified and immersed in an acetone solution containing Myline 1 at $7.10^{-4}$M. The obtained spectra are illustrated in FIG. 12. The spectra a, b, c, d, e, f, g, h and i correspond to times of 15, 30, 45, 60, 90, 180 seconds, 6, 9 and 12 minutes, respectively. They show that a peak corresponding to the formation of J aggregates may already be observed after only 15 seconds. Maximum absorption is attained for an immersion time of 3 minutes. On the other hand, the smaller peak width at half-height is obtained for a time of 12 minutes.

Application to the Detection of an Electron Acceptor Molecule

As mentioned earlier, one of the properties of the J aggregates is to allow an exciton or an electron to circulate extremely rapidly and almost without any loss of energy. Thus, if J aggregates of cyanines are excited, all the cyanine molecules will emit resonance fluorescence with strong intensity.

The present invention is based on the fact that, if an electron acceptor molecule is present in the environment of the J aggregate, the delocalized excitons in the J aggregate will be rapidly captured by the acceptor which will transform them into electron/hole pairs, which has the consequence of extinguishing the emission fluorescence.

Experiments were conducted with 1,1'-dimethyl-4,4'-bipyridinium, as an electron acceptor molecule, known as paraquat, for a use as a herbicide. Paraquat is also a powerful toxic substance, which notably attacks the central nervous system. It is therefore particularly important to be able to detect possible traces on cultures which have been treated.

Figure 13:
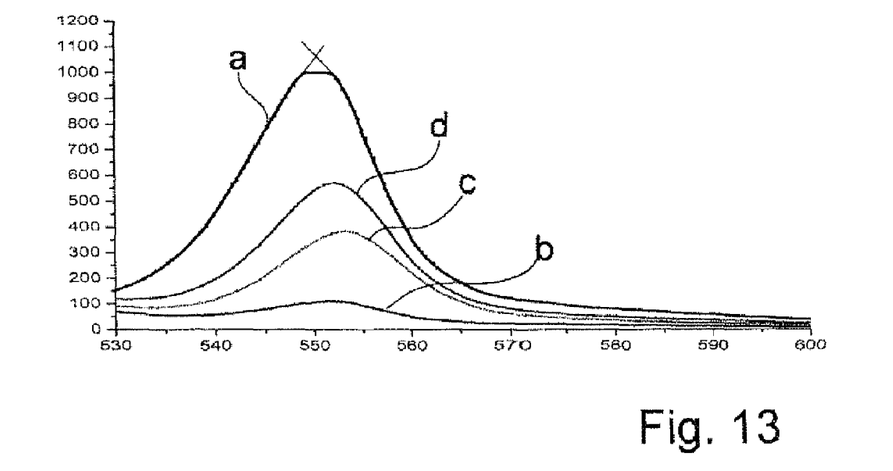
FIG. 13 is a compared spectrum of fluorescence emissions of J aggregates of Myline 1, after the latter have been put into contact with paraquat solutions of variable concentrations.

J aggregates of Myline 1 are prepared according to the method described above, on glass supports covered with a template matrix of PAMAM G4. The obtained assembly is then immersed for 1 hour in aqueous solutions of paraquat, at different concentrations. Next, the J aggregates are excited with a 510 nm wavelength source and the fluorescence emission spectra illustrated in FIG. 13 are obtained. They show the emission intensity in an arbitrary unit depending on the wavelength, for:

a: a reference sample which has not been in contact with paraquat, b: a sample having been soaked in a $4.10^{4}$M paraquat solution, c: a sample having been soaked in a $40.10^{-6}$M paraquat solution, and d: a sample having been soaked in a $1.10^{-6}$M paraquat solution.

These results actually confirm that the presence of an electron acceptor molecule may be detected by reduction of the fluorescence emission of J aggregates. The fluorescence reduction observed for a concentration of $1.10^{-6}$M is about 50%, so that it is possible to contemplate detection with still sufficient accuracy, of much smaller concentrations.

Applications to Optical Devices

Figure 14:
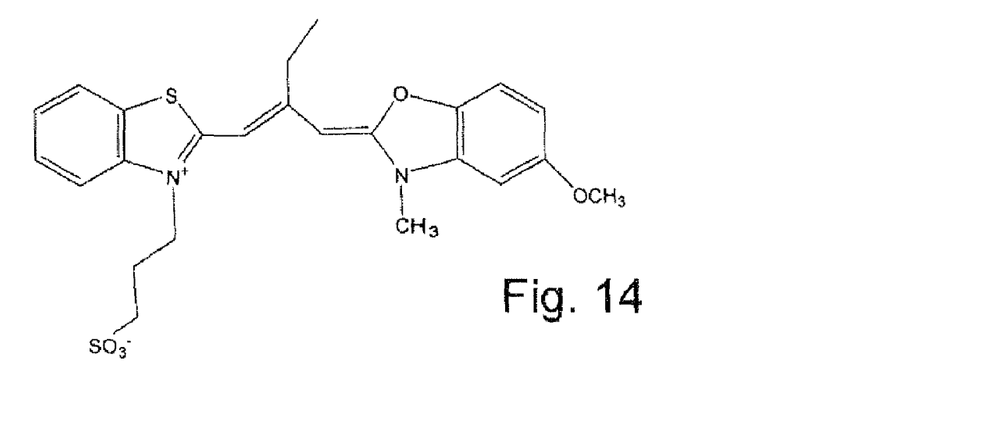
FIG. 14 shows the structure of an energy acceptor molecule.

In extension to what was mentioned above concerning the paraquat, the direct integration of an energy acceptor molecule into the actual interior of the J aggregate may be contemplated. By selecting a luminescent energy acceptor, the absorption spectrum of which covers at least partly, the emission spectrum of the aggregate, this acceptor will collect with a certain yield, the excitation energy of the aggregate and will re-emit at its own emission wavelength. For example, such an acceptor, which may be suitable for being incorporated into an aggregate of Myline 1 molecules, may be as illustrated in FIG. 14. Such a molecule has the properties required for the desired energy transfer (maximum absorption around 550 nm, emission around 600 nm).

In order to obtain a homogenous distribution of the acceptor in the J aggregate, the energy acceptor molecules are dissolved in the stock solution of cyanines used for forming the J aggregates.

Figure 15:
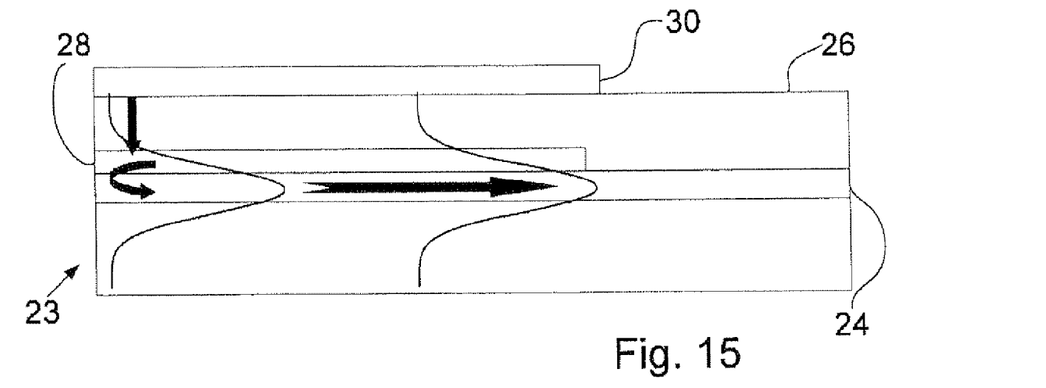
FIG. 15 is a diagram of a device provided with a source of primary light and a source of secondary light, according to the invention.

This method for using J aggregates may notably find a particularly interesting application in devices including waveguides or other optical components. Indeed, it may be desirable to integrate into such a device a light source capable of injecting a light wave into the waveguide of said device. Such integration is made possible by means of the method according to the invention. The thereby obtained device is illustrated in FIG. 15. A waveguide 24, for example in $Ta_2O_5$, is conventionally made on a glass substrate 23. By using the method of the invention, a dendrimer layer followed by a J aggregate layer, into which energy acceptor and luminescent molecules have been integrated, are then deposited on the waveguide. These thereby deposited layers, forming a secondary light source 28 are covered by a separating transparent layer 26, for example in glass. Finally, a primary light source 30 is made on the transparent layer 26 facing the source of secondary light 28. As an alternative, the separating layer may be a transparent medium such as air.

As indicated above, the energy acceptor molecules are capable of collecting the received light, at a first wavelength, from the primary source 30 and of re-emitting it at a second wavelength different from the first, into the waveguide 24. Depending on the intensity of the excitation wave, the emission at the second wavelength may either be spontaneous, or stimulated. The latter case (laser effect) occurs when the excitation at the first wavelength is sufficiently intense to cause an inversion of population of the energy acceptors, which means that more than 50% of the energy acceptors are excited at any moment.

It is particularly important that the emission wavelength of the energy acceptor be sufficiently distant from the absorption one of the J aggregates, in order to prevent the light emitted by the acceptors from being absorbed by the aggregate instead of being conducted through the waveguide. The wavelengths are for example separated by at least 20 nm, particularly from about 50 to 70 nm.

This secondary source 28 is intended to be excited by a primary light source 30 which may be positioned in several ways, as described in detail hereafter.

In the device of FIG. 15, the assembly formed by the waveguide 24 and the secondary light source 28 is integrated inside a device 23. More particularly, the secondary source 28 is covered with a transparent separator 26, for example made in glass, the primary source 30 being directly positioned on the separator 26. This primary source 30 may be a LED, an OLED or even another known light source.

Figure 16:
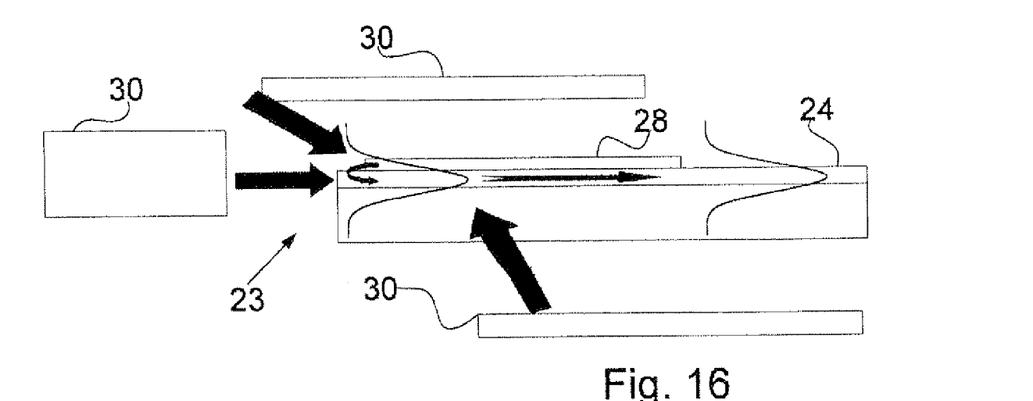
FIGS. 16 and 17 show several alternatives of a device including a secondary light source according to the invention.

In the device of FIG. 16, the assembly formed by the waveguide 24 and by the secondary light source 28 forms the upper layer of a device 23. The primary light source 30 is located at a distance from the device and may be indifferently positioned relatively to the secondary source, as shown by the different illustrated positions, as long as the light which it emits reaches the secondary source, including through the substrate and the waveguide 24 of the device 23.

Figure 17:
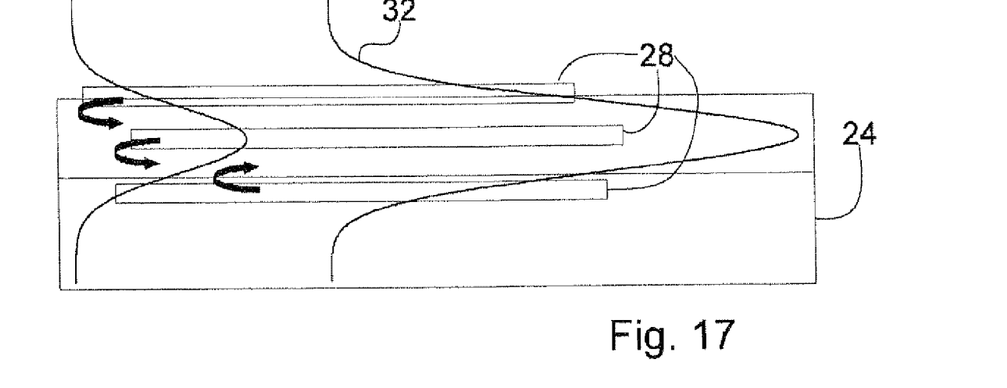

Finally, FIG. 17 proposes different alternative positions of the secondary light source 28 relatively to the waveguide 24. The profile of the transmission mode of the waveguide is illustrated in 32. The secondary source 28 may be placed anywhere inside the mode profile. In other words, it should be located in the region where the electromagnetic field of the guided wave is increased by the waveguide. It is also possible to combine several secondary sources, located at different positions, these different sources being able to absorb and/or re-emit at different wavelengths, depending on the application and the selected material.

In another alternative not shown, one skilled in the art may imagine that the luminescent acceptor is localized in a specific location of the J aggregate instead of being distributed therein in a homogenous way. In this case, when a location of the J aggregate is irradiated by a light source, the area including the acceptor will absorb the energy moving in the aggregate and only this area will emit light.

Thus, a particularly simple method is proposed with which very high quality, very stable J aggregates may be obtained and applied in industrial applications. Notably, the invention deals with one of these applications to optical devices. The techniques described above open wide perspectives in terms of experimentation in order to apply them to other hyperbranch macromolecules, to other substrates, or to other types of dyes capable of forming J aggregates. The scope of the invention is therefore not limited to the chemical species mentioned in the particular examples.

The invention claimed is:

1. A method for making J aggregates, comprising the following steps:
   i. providing a support cleaned beforehand,
   ii. depositing, on the support, a solution of dendrimer molecules capable of interacting with the support in order to form a monolayer having a regular and organized structure on an outer face of the monolayer, and
   iii. covering an obtained assembly of the support and the formed monolayer with a solution of cyanines, the solution of cyanines reacting to react with said dendrimer molecules in order to be self-arranged in J aggregates.

2. The method of claim 1, further comprising:
   before said covering step iii, positively charging the dendrimer molecules of the layer positioned on the support.

3. The method of claim 2, wherein said additional step charging consists of protonating the dendrimer molecules by a reaction in an acid medium.

4. The method of claim 1, wherein it comprises, further comprising:
   after said depositing step ii, a rinsing step for removing the dendrimer molecules which have not adhered to the support.

5. The method of claim 1, further comprising:
   after said covering step iii, a rinsing step for removing the cyanines which have not reacted with the dendrimer molecules.

6. The method of claim 1, wherein the support is made in of a material capable of interacting with said dendrimer molecules in order sufficient to allow generation of an organized layer of the dendrimer molecules.

7. The method according to claim 6, wherein said material is selected from the group consisting of glass, gold, silicon, quartz, metal oxides and polymers.

8. The method of claim 1, wherein said dendrimers are polyamido-amide (PAMAM).

9. The method of claim 1, wherein the cyanines are Mylines.

10. The method of claim 1, wherein said covering step iii of the method lasts between 5 seconds and 1 hour.

11. The method of claim 1, wherein the solution of said covering step iii is at room temperature.

12. The method of claim 1, wherein the solution of said covering step iii includes, also in solution, electron acceptors.

13. The method of claim 1, wherein the solution of said covering step iii includes, also in solution energy acceptors.

14. An assembly, comprising:
a support;
an organized layer of dendrimer molecules; and
on the organized layers of these molecules, a monolayer of molecules from the family of cyanines organized as J aggregates.

15. The assembly of claim 14, wherein the support is made on a material selected from the group consisting of glass, gold, silicon, quartz, metal oxides and polymers.

16. The assembly of claim 14, wherein said dendrimers are polyamido-amide (PAMAM) dendrimers.

17. The assembly of claim 14, wherein the cyanines are Mylines.

18. The assembly of claim 15, wherein said monolayer of molecules from the family of cyanines organized as J aggregates includes electron acceptors.

19. The assembly of claim 15, wherein monolayer of molecules from the family of cyanines organized as J aggregates includes energy acceptors.

20. The assembly of claim 19, wherein said energy acceptors are luminescent.

21. The assembly of claim 19,
wherein said monolayer of molecules from the family of cyanines organized as J aggregates absorbs energy at a first wavelength, and
wherein said acceptors emit energy at a second wavelength distant by at least 20 nm.

22. An optical device, comprising:
a waveguide and
a first light source formed with an assembly according to claim 20 and positioned in the region where the electromagnetic field of the guided wave entering the waveguide is increased by the waveguide.

23. The optical device of claim 22, wherein the waveguide is a substrate of said assembly.

24. The optical device of claim 23,
wherein said monolayer of molecules from the family of cyanines organized as J aggregates absorbs energy at a first wavelength,
wherein said acceptors emit energy at a second wavelength distant by at least 20 nm, and
further comprising: a second light source emitting said first wavelength and positioned so as to irradiate said first light source.

25. The method of claim 8, wherein said dendrimers are PAMAM dendrimers of generation 1 to 10.

26. The method of claim 25, wherein said dendrimers are PAMAM dendrimers of generation 4 to 10.

27. The assembly of claim 16, wherein said dendrimers are PAMAM dendrimers of generation 1 to 10, 28. The assembly of claim 27, wherein said dendrimers are PAMAM dendrimers of generation 4 to 10.

* * * * *